United States Patent [19]

Walker, Jr. et al.

[11] Patent Number: 4,922,000

[45] Date of Patent: May 1, 1990

[54] PRODUCTION OF DIALKYL (PHENYLENEDIOXY) DIACETATES

[75] Inventors: Theodore R. Walker, Jr.; W. Carl Wooten, Jr., both of Kingsport, Tenn.

[73] Assignee: Eastman Kodak Company, Rochester, N.Y.

[21] Appl. No.: 247,229

[22] Filed: Sep. 21, 1988

[51] Int. Cl.$^5$ .............................................. C07C 69/76
[52] U.S. Cl. .................................................... 560/061
[58] Field of Search .......................................... 560/61

[56] References Cited

U.S. PATENT DOCUMENTS 4,435,590  3/1984  Shalaby et al. ..................... 560/61
4,546,152  10/1985  Koelmel ............................. 525/437

Primary Examiner—Paul J. Killos
Attorney, Agent, or Firm—Thomas R. Savitsky; Mark A. Montgomery; William P. Heath, Jr.

[57] ABSTRACT

Disclosed is a process for preparation of dialkyl (phenylenedioxy)acetates such as dimethyl (1,3-phenylenedioxy)acetate in high yield.

The process involves controlling certain reaction conditions such as order of addition of reactants and rate of addition.

20 Claims, No Drawings

PRODUCTION OF DIALKYL (PHENYLENEDIOXY) DIACETATES

FIELD OF INVENTION

The present invention relates to production of dialkyl (phenylenedioxy)diacetates in high yield.

BACKGROUND OF THE INVENTION

Dialkyl (phenylenedioxy)diacetates such as dimethyl (1,3-phenylenedioxy)diacetate are useful for producing polymers with high gas barrier properties useful in food packaging (e.g., see U.S. Pat. No. 4,435,590, incorporated herein by reference in its entirety).

U.S. Pat. No. 4,435,590 teaches preparation of a dimethyl phenylene-bis-oxyacetate derivative by reaction of hydroquinone with chloroacetic acid in the presence of aqueous NaOH to give the diacid which is then esterified. This procedure produces a substantial amount of trifunctional impurities which must be removed for most polymer applications. Such trifunctional impurities are difficult to remove and the overall yield of desired product achieved is in the 50% range.

It would be highly desirable to have a process for production of dialkyl (phenylenedioxy)diacetates in high yield.

SUMMARY OF THE INVENTION

It has now been discovered that by controlling certain reaction conditions, such as order of addition of reactants and rate of addition, the yield of a desired dialkyl (phenylenedioxy)diacetate derivative can be vastly improved as compared to prior art processes.

More specifically, the present invention is directed to a process for preparing a compound of the formula:

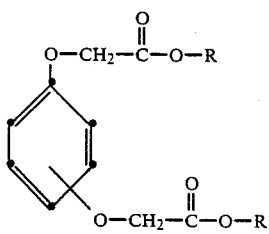

wherein R is phenyl or a straight chain, branched chain, or cyclic alkyl moiety of 1 to 12 carbon atoms, comprising adding an ionized compound of the formula:

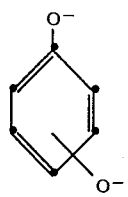

to a reaction medium comprising a haloacetate compound of the formula:

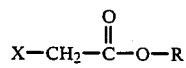

wherein R is as defined hereinabove and X is halogen, the addition occurring in the presence of a suitable solvent and over a period of time sufficiently long enough to achieve a rate of addition such that at any given time during the addition the concentration of unreacted Compound II in the reaction medium is less than 10 mole percent relative to the starting concentration of Compound III, and said process occurring under condition such that greater than 70% of the maximum theoretical yield of Compound I is formed.

A preferred process (hereinafter referred to as "the preferred process") of the present invention comprises preparing a compound of the formula:

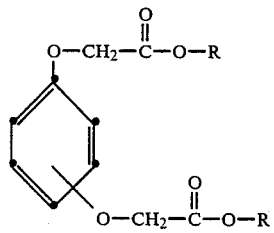

wherein R is phenyl or a straight chain, branched chain, or cyclic alkyl moiety of 1 to 12 carbon atoms, comprising the steps of (a) contacting a compound of the formula:

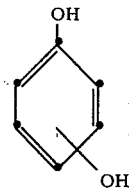

with a strong base in the presence of a suitable solvent to obtain an intermediate reaction product, and (b) adding the intermediate reaction product in solvent obtained by step (a) to a reaction medium comprising a compound of the formula:

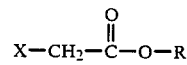

wherein R is as defined hereinabove and X is halogen, the addition occurring over a period of time greater than about 30 minutes, said process occurring under conditions such that greater than 70% of the maximum theoretical yield of Compound I is formed.

As used herein, the term "halo" or "halogen" refers to fluoro, chloro, bromo, or iodo.

DETAILED DESCRIPTION OF THE INVENTION

In the process of the present invention it is preferred that Compound I and Compound II are substituted at the meta positions. It is also preferred that the R substituent of Compound I and Compound III is an alkyl group of one to four carbon atoms, especially methyl or ethyl. It is also preferred that the X substituent of Compound II is chloro.

It is preferred that the period of time of addition is greater than about 30 minutes, more preferred is greater than about 120 minutes and less than about 5 hours.

It is preferred that the theoretical yield of Compound I is greater than 90% of the theoretical yield.

In the process of the present invention, although the use of excess haloacetate (i.e. Compound III) is not essential, it accelerates the reaction and is, therefore, preferred. The excess is easily recovered by distillation. A preferred molar proportion of Compound II:Compound III is between about 1:2 to about 1:10; and most preferred is about 1:3.5.

In the preferred process, it is preferred that the total molar proportions of Compound IV:base:Compound III is between about 1:2:2 and about 1:4:10; most preferred is about 1:2.5:3.5.

It is also preferred that Compound II is a sodium salt.

In the preferred process, most strong bases are suitable. Certain organic bases such as trialkyl amines and pyridine will not work well. The preferred bases are sodium metal and sodium alkoxides such as sodium methoxide and sodium ethoxide. NaOH may be used but the $H_2O$ produced should be removed to prevent hydrolysis of the haloacetate.

A variety of solvents, including alkyl haloacetates, may be used in the present invention; however, polar solvents are preferred. The reaction will be sluggish in nonpolar solvents due to the low solubility of diol salts in these solvents. Although water is the best solvent for resorcinol ions, it is not a desirable solvent for this reaction because it hydrolyzes the haloacetate to give glycolic ester, glycolic acid, and haloacetic acid. The preferred solvent is the alcohol corresponding to the alcoholic component of the haloacetate (i.e., Compound III). This has a twofold advantage: (1) it is usually a good solvent for both the haloacetate and the diol and (2) it usually avoids production of mixed esters which would result if a different alcohol were used.

The process of the invention will proceed satisfactorily at any temperature between about 25° and 200°. However, the higher temperatures in this range, especially above 170°, produce alkylation of the ring to give a triester, for example, of the type

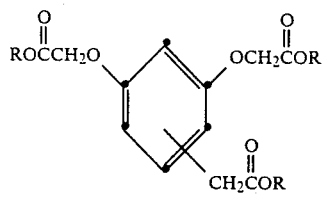

It is preferred that the process of the invention proceed such that less than about 1% of the theoretical maximum of triester is formed. It is also preferred that the purity of the desired product is greater than 90%, preferred is greater than 95% and most preferred is greater than 99%.

It is preferred that the process of the invention take place in the absence of, or substantial absence of, oxygen. This can be accomplished by blanketing the reaction medium during reaction with an inert gas such as nitrogen or argon. While the reaction will function in the presence of oxygen, the product is more highly colored.

The following examples are to illustrate the invention but should not be interpreted as a limitation thereon.

EXAMPLES

Example 1

Addition of Resorcinol Salt to Chloroacetate

This example illustrates the process of the present invention. Methyl chloroacetate, 380 grams (g) (3.5 moles), is placed in a dry 2-liter (L) flask equipped with a dry 2-L dropping funnel, $N_2$ inlet, heating mantle, thermometer, mechanical stirrer, and a reflux condenser topped with drying tube. The flask is purged with $N_2$ and kept under a $N_2$ blanket throughout the reaction. The methyl chloroacetate is heated at 80°–100° C. Resorcinol, 110 (g) (1.0 moles is dissolved in 1100 milliliters (mL) methanol and placed in the dropping funnel. Sodium, 46 g (2.0 moles), or an equivalent amount of sodium methoxide in methanol is added gradually to the resorcinol solution. The resorcinol salt solution is added dropwise over at least 3 hours to the stirring methyl chloroacetate. The reaction temperature drops gradually to the reflux temperature of methanol. When the addition is complete, 23 g more Na dissolved in 400 mL methanol is added dropwise to the refluxing mixture. Afterwards, it is refluxed 6 hours longer. Gas chromatography shows 96% conversion of resorcinol to product. The mixture is filtered hot to remove NaCl. Methanol is removed from the filtrate in a rotary evaporator under house vacuum. Afterwards, the vacuum is increased to 1–2 millimeters (mm) to remove methyl chloroacetate. The resulting syrup is dissolved in 300 mL methanol with warming and filtered to clarify. The filtrate is cooled to 0°–5° C. and filtered. The filter cake is washed with a small amount of cold ethanol and dried under vacuum at room temperature. The yield is 228 g (90% yield). The purity as shown by gas chromatography (GC) is 98.1%.

This product can be further purified by distilling through a 6-inch (in.) Vigreux column. Boiling point (Bp) is 152–153 at 0.25 mm. This gives 208 g (91% distilled yield) in 99.6% purity.

Example 2

Addition of Chloroacetate to Resorcinol Salt

Sodium metal, 26 g (1.13 mole) is dissolved in 1,000 milliliters (mL) methanol in a three-neck flask equipped with thermometer, $N_2$ inlet, stirrer, reflux condenser, and dropping funnel. The solution is blanketed with $N_2$. Resorcinol, 55 g (0.5 mole), is dissolved in 200 mL methanol and added through the dropping funnel to the $NaOCH_3$ solution. The mixture is stirred about 10 minutes longer and 130 grams (g) (1.2 mol) methyl chloroacetate is added in one portion. The mixture is refluxed 10 hours. Gas chromatography of the reaction mixture shows 53% conversion of resorcinol to dimethyl (1,3-phenylenedioxy)diacetate. The addition of 5 g (0.217 mole) Na to the mixture raises the conversion from 53% to 62%. The addition of 10 g (0.43 mole) Na and 10 hours longer refluxing raises the conversion to 73%.

When Examples 1 and 2 are compared, it can be seen that the process of Example 1 gives much greater conversion of resorcinol to product, 96% versus 73%. Also the high conversion of Example 1 is achieved without the successive additions of excess base that were employed in Example 2.

Example 3

This example illustrates the process of U.S. Pat. No. 4,435,590. A three-litre, three-neck flask, condenser, and dropping funnel were flushed with $N_2$ overnight to remove adsorbed moisture. To the flask was charged 110 g (1 mole) resorcinol, 217 g (2 moles) methyl chloroacetate, and 575 mL methanol. A blanket of $N_2$ was maintained throughout the system during the reaction. The mixture was refluxed. Na, 51 g (2.2 moles) was dissolved in 1 L methanol in the dropping funnel. The resulting sodium methoxide solution was added dropwise over a period of approximately one hour. Afterwards the reaction mixture was refluxed an additional 17 hours. The mixture was filtered hot to remove NaCl. The filtrate was cooled to 0°–5° C. in an ice bath and filtered to give a dry weight of 95.6 g or 38% yield.

U.S. Pat. No. 4,435,590 does not provide a yield or an example for this compound. However, it does provide an example for the analogous compound made from hydroquinone and reports a yield of 55% after two additional recrystallizations. The process, therefore, gives a much lower yield for the 1,3 isomer than for the 1,4 isomer.

When Examples 1 and 3 are compared, it can be seen that the process of Example 1 gives a much greater yield, 90% versus 38%.

Example 4

The procedure of Example 2 is repeated with n-butanol as solvent instead of methanol and with a higher reflux temperature (116° C. versus 68° C.). After 6 hours reflux time, there is 61% conversion of resorcinol to product. The addition of 0.1 mole Na and 0.1 mole chloroacetate raised the conversion to only 67%.

Example 5

The procedure of Example 4 is repeated with sodium methoxide as base instead of sodium metal and ethyl chloroacetate instead of methyl chloroacetate. After six hours reflux time, there is 61% conversion of resorcinol to product, the same conversion obtained in Example 3. After 21 hours refluxing, the conversion is unchanged. The addition of 0.22 mol NaOCH$_3$ and 0.2 mol chloroacetate raises the conversion to 74%.

The reaction mixture is filtered to remove NaCl, and the filtrate is distilled to give 121 g (71% yield) in 96% purity (GC). Recrystallization from methanol gives 95 g (56% yield) of desired product in 99% purity.

Example 6

Example 4 is repeated except that NaOH is used as base and the water formed is azeotroped with butanol before chloroacetate is added. After refluxing 30 minutes, the conversion to product is 50%. After refluxing 30 minutes longer, the conversion is unchanged.

Example 7

The procedure of Example 2 is followed with pyridine as base and CHCl$_3$ as solvent. There is no conversion to product.

Example 8

The procedure of Example 2 is followed with triethylamine as base and CHCl$_3$ as solvent. There is no conversion to product.

Example 9

The procedure of Example 2 is followed with N-methyl-pyrrolidinone as solvent. At 125°, 78% conversion to desired product is obtained in 30 minutes. When the temperature is raised to 170°, the conversion declines to 63% over 12 hours.

Example 10

The procedure of Example 2 is followed with NaOCH$_3$ as base and N,N-dimethylformamide as solvent. Reaction temperature is 110°–120° C. The conversion to product is 51%. The addition of 50% excess base and 45% excess chloroacetate raises the conversion to 89%. NaCl is removed by filtration, and the filtrate is distilled to give 85% yield in 85% purity (GC). Redistillation gives 61% yield in 95% purity, still too impure for polymer use.

We claim:

1. A process for preparing a compound of the formula:

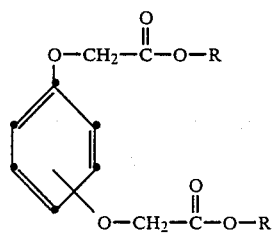

wherein R is phenyl or a straight chain, branched chain, or cyclic alkyl moiety of 1 to 12 carbon atoms, comprising adding an ionized compound of the formula:

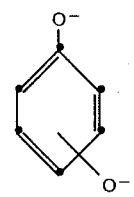

to a reaction medium comprising a haloacetate compound of the formula:

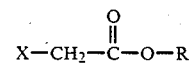

wherein R is as defined hereinabove and X is halogen, the addition occurring in the presence of a suitable solvent and over a period of time sufficiently long enough to achieve a rate of addition such that at any given time during the addition the concentration of unreacted Compound II in the reaction medium is less than 10 mole percent relative to the starting concentration of Compound III, and said process occurring under condition such that greater than 70% of the maximum theoretical yield of Compound I is formed.

2. A process for preparing a compound of the formula:

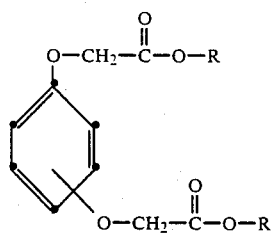

wherein R is phenyl or a straight chain, branched chain, or cyclic alkyl moiety of 1 to 12 carbon atoms, comprising the steps of (a) contacting a diol compound of the formula:

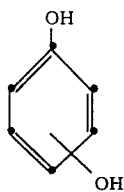

with a strong base in the presence of a suitable solvent to obtain an intermediate reaction product, and (b) adding the intermediate reaction product in solvent obtained by step (a) to a reaction medium comprising a compound of the formula:

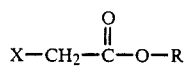

wherein R is as defined hereinabove and X is halogen, the addition occurring over a period of time greater than about 30 minutes, said process occurring under conditions such that greater than 70% of the maximum theoretical yield of Compound I is formed.

3. The process of claim 1 wherein the period of time of addition is greater than about 30 minutes.

4. The process of claim 1 wherein the period of time of addition is greater than about 120 minutes and less than about 5 hours.

5. The process of claim 2 wherein the period of time of addition is greater than about 120 and less than about 5 hours.

6. The process of claim 1 wherein greater than 90% of the maximum theoretical yield of Compound I is formed.

7. The process of claim 2 wherein greater than 90% of the maximum theoretical yield of Compound I is formed.

8. The process of claim 1 wherein the total molar proportion of Compound II:Compound III is between about 1:2 to about 1:10.

9. The process of claim 1 wherein the total molar proportion of Compound II:Compound III is about 1:3.5.

10. The process of claim 2 wherein the total molar proportions of Compound II:base:Compound III is between about 1:2:2 and about 1:4:10.

11. The process of claim 2 wherein the total molar proportions of Compound IV:base:Compound III is about 1:2.5:3.5.

12. The process of claim 1 wherein Compound I and Compound II are substituted at the meta positions.

13. The process of claim 2 wherein Compound I and Compound IV are substituted at the meta positions.

14. The process of claim 1 wherein R is methyl or ethyl and X is chloro.

15. The process of claim 2 wherein R is methyl or ethyl and X is chloro.

16. The process of claim 1 wherein Compound II is a sodium salt.

17. The process of claim 2 wherein the strong base is selected from the group consisting of sodium metal, sodium alkoxide and sodium hydroxide.

18. The process of claim 1 wherein the suitable solvent is the alcohol corresponding to the alcoholic component of the haloacetate of Compound III.

19. The process of claim 2 wherein the suitable solvent is the alcohol corresponding to the alcoholic component of the haloacetate of Compound III.

20. The process of claim 2 wherein R is methyl, X is chloro, the strong base is sodium methoxide, and the suitable solvent is methanol.

* * * * *